United States Patent
Baldi et al.

(10) Patent No.: US 8,118,923 B2
(45) Date of Patent: Feb. 21, 2012

(54) PROCESS FOR FUNCTIONALIZING TITANIUM METAL SURFACES WITH NANOMETRIC PARTICLES OF TITANIUM AND PRODUCTS THUS FUNCTIONALIZED

(75) Inventors: Giovanni Baldi, Montespertoli (IT); Marco Bitossi, Montelupo Fiorentino (IT); Andrea Barzanti, Montelupo Fiorentino (IT)

(73) Assignee: Colorobbia Italia S.p.A., Sovigliana Vinci (IT)

( * ) Notice: Subject to any disclaimer, the term of this patent is extended or adjusted under 35 U.S.C. 154(b) by 656 days.

(21) Appl. No.: 12/278,069

(22) PCT Filed: Feb. 2, 2007

(86) PCT No.: PCT/EP2007/051030
§ 371 (c)(1),
(2), (4) Date: Aug. 1, 2008

(87) PCT Pub. No.: WO2007/088199
PCT Pub. Date: Aug. 9, 2007

(65) Prior Publication Data
US 2009/0114124 A1    May 7, 2009

(30) Foreign Application Priority Data
Feb. 3, 2006    (IT) .................. FI2006A0034

(51) Int. Cl.
C09C 1/36 (2006.01)
B05D 1/18 (2006.01)
B05D 3/02 (2006.01)

(52) U.S. Cl. .................. 106/436; 427/435; 427/374.3

(58) Field of Classification Search .................. 106/436, 106/287.1; 427/435, 443.2, 374.1–374.6
See application file for complete search history.

(56) References Cited

FOREIGN PATENT DOCUMENTS

| WO | 93/21969 A1 | 11/1993 |
|---|---|---|
| WO | 2004/026346 A2 | 4/2004 |
| WO | 2004/103423 A1 | 12/2004 |
| WO | 2006/061367 A1 | 6/2006 |
| WO | 2007/088151 A1 | 8/2007 |

OTHER PUBLICATIONS

Addamo, Maurizio et al., "Preparation, Characterization, and Photoactivity of Polycrystalline Nanostructured TiO2 Catalysts," J. Phys. Chem. B 2004, 108, 3303-3310.

*Primary Examiner* — Anthony J Green
*Assistant Examiner* — Pegah Parvini
(74) *Attorney, Agent, or Firm* — Stradley Ronon Stevens & Young LLP

(57) ABSTRACT

A method is described which enables antibacterial properties to be attributed to a titanium surface by applying titanium dioxide suspensions of nanometric dimensions.

21 Claims, No Drawings

PROCESS FOR FUNCTIONALIZING TITANIUM METAL SURFACES WITH NANOMETRIC PARTICLES OF TITANIUM AND PRODUCTS THUS FUNCTIONALIZED

FIELD OF THE INVENTION

The present invention relates to the field of titanium metal surface treatment.

STATE OF THE ART

In recent times, titanium has been widely utilized in the manufacture of parts used in implantology (particularly in the orthodontic field). In view of this use, the ability of the surfaces of the various constituent parts of such implants to perform a bactericidal and/or bacteriostatic action is evidently important.

Italian patent application FI2004A000252 (in the name of the same applicant) describes a process for preparing titanium oxide in nanoparticle form and the relative dispersions obtained by said process, consisting of nanometric particles of titanium oxide suspended in a mixture of water and a suitable complexing solvent (such as polyethylene glycol). The aforesaid patent application also mentions the usefulness of said suspensions for preparing photocatalytic coatings.

Similarly, Italian patent FI2006A000030 describes a process for preparing titanium oxide in nanoparticle form in an aqueous dispersion and the relative dispersions themselves.

SUMMARY OF THE INVENTION

The present invention refers to a process for functionalizing titanium metal surfaces with nanometric particles of titanium wherein:
 the article to be functionalized is immersed in a suspension of nanometric particles of titanium dioxide;
 when completely wetted the article is heated to remove the solvent;
 the article is subjected to a thermal cycle in order to improve fixing of the nanoparticles to the treated surface.

DETAILED DESCRIPTION OF THE INVENTION

It has now been surprisingly found that dispersions of nanometric particles of titanium oxide as described in the aforesaid patent applications lend themselves in particular to the treatment of titanium surfaces, enabling them to exert a bactericidal or bacteriostatic action which is found to be extremely useful and interesting in the case of prostheses, or parts thereof, particularly orthodontic parts formed of this metal.

As is more amply illustrated in patent application FI2004A000252 the process for preparing dispersions of anatase $TiO_2$ particles usable in the present invention, comprises the following stages:
i) reacting a titanium alkoxide with a suitable complexing solvent;
ii) distilling the solution derived from step i) until a small quantity results;
iii) adding water together with said complexing solvent and one or more polycondensation inhibitors to the solution derived from step ii), then heating the reaction mixture under reflux, to obtain the desired nanoparticulate dispersion.

The titanium alkoxide is preferably chosen from the group consisting of titanium methoxide, ethoxide, normal-propoxide, isopropoxide, normal-butoxide, and isobutoxide, being preferably titanium isopropoxide.

The complexing solvents typically used in the present process are polyethylene glycols, having molecular weights for example of between 200 and 600. Longer chain polyethylene glycols of molecular weight up to 10,000 can also be used, diethylene glycol being preferred.

The term "polycondensation inhibitor" means typically a mixture comprising at least one mineral acid and one organic acid, where the mineral acid can be chosen for example from the group consisting of hydrochloric acid, nitric acid, sulfuric acid, perchloric acid, hydrobromic acid and hydriodic acid, and the organic acid is preferably acetic acid; the polycondensation inhibitor is preferably a mixture of hydrochloric acid and acetic acid.

The quantity of polycondensation inhibitor added is such that the mineral acid quantity is between 0.1 and 10% by volume on the total volume of the reaction mixture, while the organic acid quantity is between 1 and 20% by volume on the total volume of the reaction mixture.

The aforesaid patent application FI2006A000030 also amply illustrates and claims a process for preparing dispersions of anatase $TiO_2$ particles in water.

According to this process a titanium salt is reacted in water under hot conditions in the presence of mineral acids and a non-ionic surfactant, the solution thus obtained being then possibly reduced to a small quantity. Both the general and preferred definitions of titanium salt and mineral acid, already aforegiven for the process of patent application FI2004A00025, are valid, whereas "non-ionic surfactants" mean those possessing an ether or ester type polar function, being preferably Triton X-100 (TX-100).

The molar ratio of titanium alkoxide to acid is between 0.005 and 15, preferably between 5 and 6, while the reaction temperature is normally between 15 and 95° C. preferably 45-55° C. and the reaction times are between 12 and 72 hours, being preferably 24 hours.

Furthermore, as described in both applications, in both the above cases Ti can be doped with a metal chosen from the transition metal series and particularly from Ag, Cu and Ce by the addition a salt thereto in step i) or alternatively in step iii) of the present process. In this manner, the process will lead to the formation of a $TiO_2$ dispersion doped with Ag, Cu or Ce, able to exhibit its own catalytic activity even without UV light irradiation.

An illustrative example for preparing the suspensions used in the present invention both comprising the complexing agent and in aqueous suspension (examples already given in the aforesaid patent applications) are given hereinafter.

EXAMPLES

Preparation of a Nanoparticulate Dispersion of Anatase $TiO_2$ in Water/diethylene Glycol Starting from Ti Isopropoxide

Example 1

5.53 liters of diethylene glycol are fed into a 20 liter flask to which are added 5.54 liters of titanium isopropoxide. The reaction mixture is maintained under agitation for 5 minutes then heated to 120° C. to distil off the isopropyl alcohol formed, until a small quantity results. 11.1 liters of diethylene glycol, 125 ml of 32-33% hydrochloric acid (w/w), 2.07 liters of glacial acetic acid and 125 ml of deionized water are added;

the temperature is brought to 180° C. and the mixture maintained under reflux for 2 hours.

Example 2

5 g of concentrated HCl, 75 g of TX-100 and water to make up to 750 g in weight are placed into a 2 liter reactor heated with circulating diathermic oil in an external jacket. The temperature is brought to 50° C. 50 g of Ti[OCH(CH$_3$)$_2$]$_4$ (TIP) are then added very quickly and the formation of a white flocculate precipitate is immediately noted.

After 7 hours a very stable transparent sol is formed.

The suspensions thus obtained are then used to functionalize the surface of titanium metal parts.

In particular the article to be functionalized is immersed in the suspension and possibly rotated so as to completely wet the surface therewith. It is then heated and finally subjected to a thermal cycle in order to improve the fixing of nanoparticles onto the treated surface.

The suspensions used for the initial bath generally contain from 0.1% to 15%, preferably 1%, of nanometric titanium dioxide, and possibly from 0.005% to 0.5%, preferably 0.05%, of silver, the percentages being calculated by weight on the solution. The sole function of the initial heating is to accelerate solvent removal and can be undertaken for example in an oven at around 120° C.

The subsequent thermal cycle comprises an increasing temperature gradient between 0.1 and 10° C./minute starting from ambient temperature up to a temperature of between 400° and 850° C. which is maintained for a time between 30 and 240 minutes, the treated article being allowed to cool down freely to ambient temperature.

The process in accordance with the present invention can be undertaken on ground surfaces but, if preferred, the surface can be subjected to mordanting in accordance with normally employed techniques for this purpose, prior to immersion in the titanium dioxide suspension.

Some examples are described hereinafter for treating a titanium article in accordance with the invention with the aim of attributing thereto the desired bactericidal properties.

Example 3

A titanium screw for orthodontic implants was subjected to mordanting with mixtures of acids (a known process in the state of the art) in order to obtain a structured non-smooth surface. This was immersed into a formulated product in diethylene glycol containing 1% by weight of nanoparticulate titanium dioxide and kept under rotation for 5 seconds.

The screw was then placed in an oven at 120° C. for 1 hour in order to promote solvent evaporation. In this step the titanium dioxide nanoparticles deposit onto the surface of the screw. The screw is then treated at high temperature to stably fix the nanoparticles to the metal. The thermal cycle consists of a heating ramp up to 650° C. lasting 2 hours, a plateau of 2 hours, then free cooling to ambient temperature.

Example 4

A ground titanium screw for orthodontic implants was immersed in a formulated product in diethylene glycol containing nanoparticulate silver adsorbed onto nanoparticulate titanium dioxide for a total content of 1% of titanium dioxide and 0.05% of nanoparticulate silver and kept under rotation for 5 seconds.

The screw was then placed in an oven at 120° C. for 1 hour in order to promote solvent evaporation. In this step the titanium dioxide nanoparticles deposit onto the surface of the screw. The screw is then treated at high temperature to stably fix the nanoparticles to the metal. The thermal cycle consists of a heating ramp up to 650° C. lasting 2 hours, a plateau of 2 hours, then free cooling to ambient temperature.

Example 5

A mordanted titanium screw for orthodontic implants was immersed in a formulated product in water containing nanoparticulate silver adsorbed onto nanoparticulate titanium dioxide for a total content of 0.1% of titanium dioxide and 0.005% of nanoparticulate silver and kept under rotation for 5 seconds.

The screw was then placed in an oven at 120° C. for 1 hour in order to promote solvent evaporation. In this step the titanium dioxide nanoparticles deposit onto the surface of the screw. The screw is then treated at high temperature to stably fix the nanoparticles to the metal. The thermal cycle consists of a heating ramp up to 750° C. lasting 2 hours, a plateau of 2 hours, then free cooling to ambient temperature.

Example 6

An aqueous solution of nanoparticulate titanium dioxide containing 1% by weight of the oxide was sprayed onto one side of a small smooth titanium plate. The small plate is dried in an oven at 120° C. for 1 hour in order to promote solvent evaporation. The small plate is then treated at high temperature to fix the nanoparticles to the metal. The thermal cycle consists of a heating ramp up to 800° C. lasting 2 hours, a plateau of 2 hours, then free cooling to ambient temperature.

The invention claimed is:

1. A process for functionalizing a titanium metal surface with nanometric particles of $TiO_2$, the process comprising:
    immersing an article having a surface comprising titanium metal in the nanometric suspension of anatase $TiO_2$ produced by:
        i) reacting a titanium alkoxide with a polyethylene glycol;
        ii) heating the solution derived from step i) to remove at least a portion of any alcohol formed as a product of the reacting step;
        iii) adding a composition comprising water, a polyethylene glycol, and a polycondensation inhibitor to the solution derived from step ii), wherein the polycondensation inhibitor comprises a mixture of at least one mineral acid and at least one organic acid; and
        iv) heating the composition of step iii) under reflux to obtain the nanometric suspension of anatase $TiO_2$;
    removing the article from the suspension and heating the article to dry the article; and
    subjecting the article to a thermal cycle, wherein the thermal cycle comprises:
        subjecting the article to a rising temperature gradient of between 0.1 and 10° C./minute starting from ambient temperature up to a target temperature of between 400° and 850° C.;
        maintaining the target temperature for a period between 30 and 240 minutes; and
        cooling the article to ambient temperature.

2. The process of claim 1 wherein the polyethylene glycol is diethylene glycol.

3. The process of claim 1 wherein the mineral acid is selected from the group consisting of hydrochloric acid, nitric acid, sulfuric acid, perchloric acid, hydrobromic acid, and hydroiodic acid.

4. The process of claim 1 wherein the organic acid is acetic acid.

5. The process of claim 1 wherein the polycondensation inhibitor comprises a mixture of hydrochloric acid and acetic acid.

6. The process of claim 1 wherein the titanium alkoxide is selected from the group consisting of titanium methoxide, titanium ethoxide, titanium n-propoxide, titanium isopropoxide, titanium n-butoxide, and titanium isobutoxide.

7. The process of claim 6 wherein the titanium alkoxide is titanium isopropoxide.

8. The process of claim 1 wherein the surface of the article is mordanted prior to the immersing step.

9. The process of claim 1 wherein the suspension comprises between 0.1% and 15% of nanometric $TiO_2$.

10. The process of claim 9 wherein the suspension comprises 1% of nanometric $TiO_2$.

11. The process of claim 1 wherein the suspension further comprises between 0.005% and 0.5% of silver.

12. The process of claim 11 wherein the suspension comprises 0.05% of silver.

13. The process of claim 1 wherein the article is a prostheses for orthodontic applications.

14. A process for functionalizing titanium metal surfaces with nanometric particles of titanium comprising:
    immersing an article to be functionalized in a suspension of nanometric particles of titanium dioxide;
    completely wetting the article;
    heating the article to remove solvent;
    subjecting the article to a thermal cycle to improve fixing of the nanometric particles to a treated surface; and
    obtaining a suspension of nanometric particles of titanium dioxide by:
        reacting a titanium alkoxide with a suitable complexing solvent to form a solution;
        distilling the solution;
        adding water together with the complexing solvent and one or more polycondensation inhibitors to the solution; and
        heating the reaction mixture under reflux to obtain a nanoparticulate dispersion.

15. The process according to claim 14 wherein the thermal cycle comprises:
    subjecting the article to a rising temperature gradient of between 0.1 and 10° C./minute starting from ambient temperature up to a target temperature of between 400° C. and 850° C.;
    maintaining the target temperature for a period of between 30 and 240 minutes; and
    cooling the article to ambient temperature.

16. The process of claim 14 wherein the surface of the article is mordanted prior to the immersing step.

17. The process of claim 14 wherein the suspension comprises between 0.1% and 15% of nanometric $TiO_2$.

18. The process of claim 14 wherein the suspension comprises 1% of nanometric $TiO_2$.

19. The process of claim 14 wherein the suspension further comprises between 0.005% and 0.5% of silver.

20. The process of claim 19 wherein the suspension comprises 0.05% of silver.

21. The process of claim 14 wherein the article is a prostheses for orthodontic applications.

* * * * *